United States Patent
Matsumoto

(10) Patent No.: US 10,704,022 B2
(45) Date of Patent: Jul. 7, 2020

(54) CELL EVALUATION APPARATUS AND CELL EVALUATION METHOD

(71) Applicant: FUJIFILM Corporation, Tokyo (JP)

(72) Inventor: Tsuyoshi Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 216 days.

(21) Appl. No.: 15/916,609

(22) Filed: Mar. 9, 2018

(65) Prior Publication Data

US 2018/0195038 A1      Jul. 12, 2018

Related U.S. Application Data

(63) Continuation of application No. PCT/JP2016/076812, filed on Sep. 12, 2016.

(30) Foreign Application Priority Data

Sep. 29, 2015    (JP) .................................. 2015-190860

(51) Int. Cl.
  *C12N 5/00* (2006.01)
  *G01N 33/50* (2006.01)
  (Continued)

(52) U.S. Cl.
  CPC ............. *C12N 5/0081* (2013.01); *C12M 1/00* (2013.01); *C12M 1/34* (2013.01); *C12M 41/36* (2013.01);
  (Continued)

(58) Field of Classification Search
  CPC ......... C12N 5/0081; C12M 1/00; C12M 1/34; C12M 41/36; G01N 33/48; G01N 33/5005; G06T 7/0012
  See application file for complete search history.

(56) References Cited

U.S. PATENT DOCUMENTS

2008/0144915 A1*   6/2008   Wong ................. G06K 9/00147
                                                        382/133
2009/0206234 A1*   8/2009   Okuda ..................... G01J 3/46
                                                        250/201.2
(Continued)

FOREIGN PATENT DOCUMENTS

JP       2005-168360 A       6/2005
JP        2006-42663 A       2/2006
(Continued)

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/076812, dated Apr. 12, 2018, with an English translation.

(Continued)

*Primary Examiner* — David F Dunphy
(74) *Attorney, Agent, or Firm* — Birch, Stewart, Kolasch & Birch, LLP

(57) ABSTRACT

Provided are a cell evaluation apparatus and a cell evaluation method capable of preventing overlooking of remaining undifferentiated cells. A first evaluation part 1 and a second evaluation part 2 that evaluate cells to be evaluated are provided. The first evaluation part 1 includes first and second discrimination parts 31 and 32 that respectively discriminate whether the cells to be evaluated correspond to two types of cells on the basis of an image obtained by imaging the cells to be evaluated, and the second evaluation part 2 evaluates the cells to be evaluated under an evaluation condition different from an evaluation condition of the first evaluation part in a case where discrimination results in the first and second discrimination parts 31 and 32 are conflicting.

20 Claims, 4 Drawing Sheets

| DISCRIMINATION RESULT IN FIRST DISCRIMINATION PART | DISCRIMINATION RESULT IN SECOND DISCRIMINATION PART | DISCRIMINATION RESULT |
|---|---|---|
| UNDIFFERENTIATED CELLS ARE PRESENT | DIFFERENTIATED CELLS ARE NOT PRESENT | UNDIFFERENTIATED CELLS |
| UNDIFFERENTIATED CELLS ARE NOT PRESENT | DIFFERENTIATED CELLS ARE PRESENT | DIFFERENTIATED CELLS |
| UNDIFFERENTIATED CELLS ARE PRESENT | DIFFERENTIATED CELLS ARE PRESENT | OBSCURE |
| UNDIFFERENTIATED CELLS ARE NOT PRESENT | DIFFERENTIATED CELLS ARE NOT PRESENT | OBSCURE |

(51) Int. Cl.
*G06T 7/00* (2017.01)
*C12M 1/34* (2006.01)
*C12M 1/00* (2006.01)
*G01N 33/48* (2006.01)
*C12N 5/0735* (2010.01)
*C12N 5/074* (2010.01)
*G02B 21/00* (2006.01)

(52) U.S. Cl.
CPC ......... *G01N 33/48* (2013.01); *G01N 33/5005* (2013.01); *G06T 7/0012* (2013.01); *C12N 5/0606* (2013.01); *C12N 5/0607* (2013.01); *C12N 5/0696* (2013.01); *G02B 21/0056* (2013.01); *G06T 2207/10056* (2013.01); *G06T 2207/20021* (2013.01); *G06T 2207/30024* (2013.01)

(56) References Cited

U.S. PATENT DOCUMENTS

| | | | |
|---|---|---|---|
| 2012/0142005 A1 | 6/2012 | Hosoya et al. | |
| 2014/0030729 A1* | 1/2014 | Basiji | G01N 33/57492 435/6.14 |
| 2014/0247972 A1* | 9/2014 | Wang | G06K 9/6227 382/133 |
| 2015/0124082 A1 | 5/2015 | Kato et al. | |
| 2015/0131889 A1 | 5/2015 | Aragaki | |
| 2016/0161464 A1 | 6/2016 | Tsujimoto | |

FOREIGN PATENT DOCUMENTS

| | | |
|---|---|---|
| JP | 2011-229413 A | 11/2011 |
| JP | 2014-29287 A | 2/2014 |
| JP | 2014-44050 A | 3/2014 |
| WO | WO 2010/137722 A1 | 12/2010 |
| WO | WO 2011/088091 A1 | 7/2011 |
| WO | WO 2015/025506 A1 | 2/2015 |
| WO | WO 2015/025507 A1 | 2/2015 |
| WO | WO 2015/133185 A1 | 9/2015 |
| WO | WO 2015/133187 A1 | 9/2015 |
| WO | WO 2015/146064 A1 | 10/2015 |
| WO | WO 2015/182381 A1 | 12/2015 |
| WO | WO 2015/182382 A1 | 12/2015 |
| WO | WO 2015/182396 A1 | 12/2015 |

OTHER PUBLICATIONS

International Search Report and English translation (Form PCT/ISA/210) for Application No. PCT/JP2016/076812, dated Dec. 13, 2016.

* cited by examiner

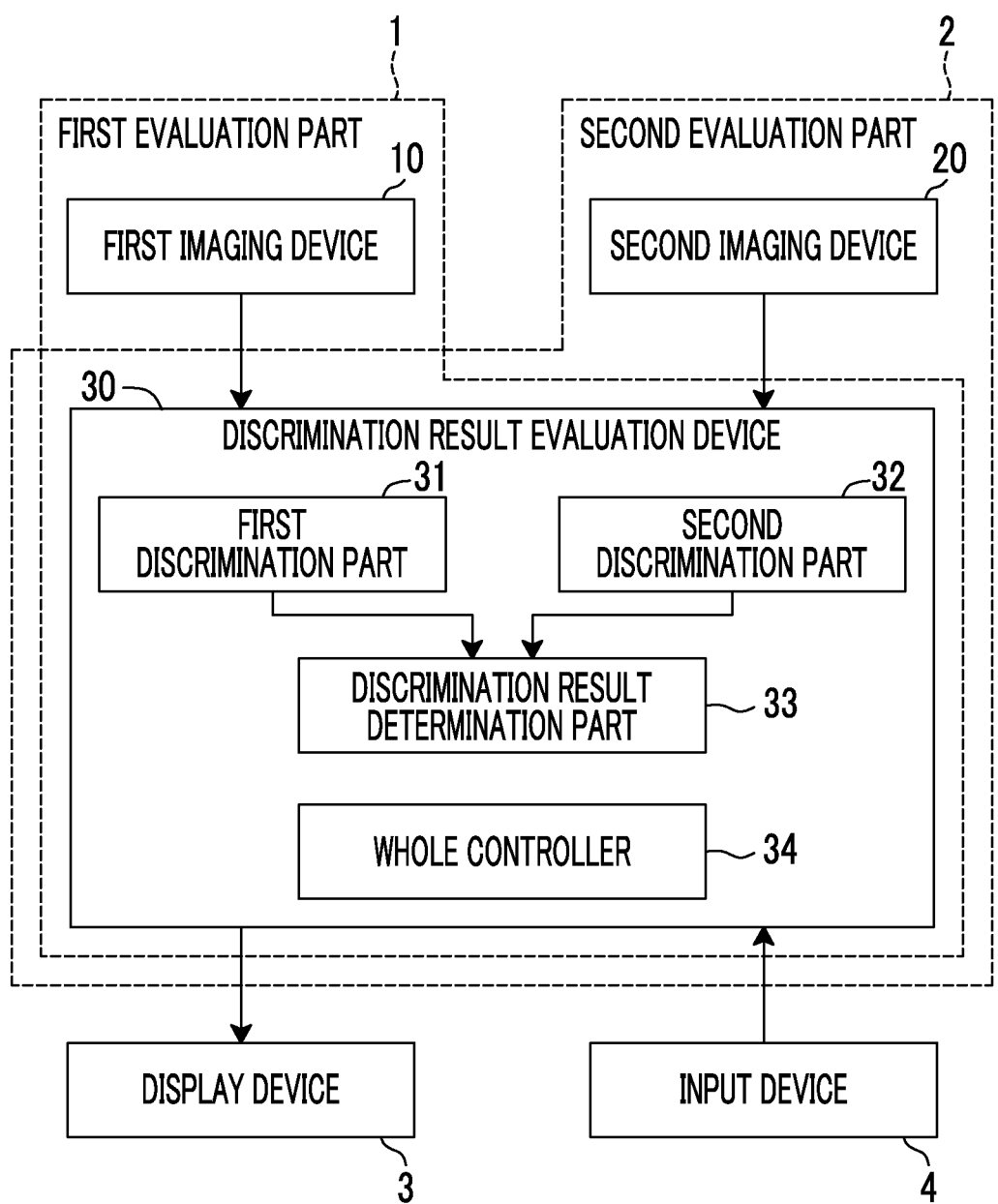

FIG. 2

| DISCRIMINATION RESULT IN FIRST DISCRIMINATION PART | DISCRIMINATION RESULT IN SECOND DISCRIMINATION PART | DISCRIMINATION RESULT |
|---|---|---|
| UNDIFFERENTIATED CELLS ARE PRESENT | DIFFERENTIATED CELLS ARE NOT PRESENT | UNDIFFERENTIATED CELLS |
| UNDIFFERENTIATED CELLS ARE NOT PRESENT | DIFFERENTIATED CELLS ARE PRESENT | DIFFERENTIATED CELLS |
| UNDIFFERENTIATED CELLS ARE PRESENT | DIFFERENTIATED CELLS ARE PRESENT | OBSCURE |
| UNDIFFERENTIATED CELLS ARE NOT PRESENT | DIFFERENTIATED CELLS ARE NOT PRESENT | OBSCURE |

FIG. 3

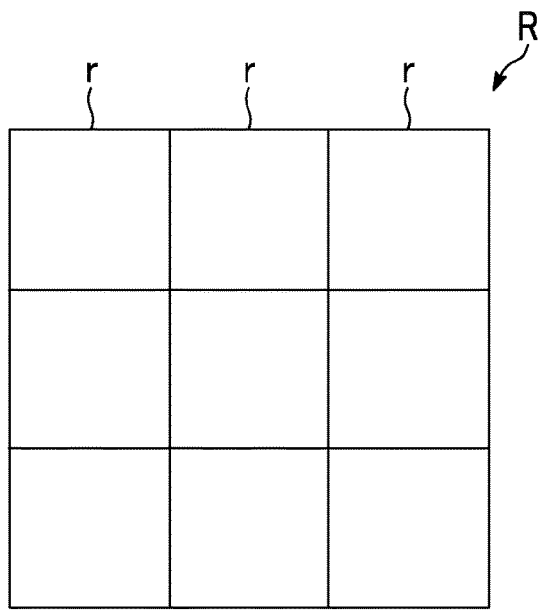

CELL EVALUATION APPARATUS AND CELL EVALUATION METHOD

CROSS-REFERENCE TO RELATED APPLICATIONS

This application is a Continuation of PCT International Application No. PCT/JP2016/076812 filed on Sep. 12, 2016, which claims priority under 35 U.S.C. § 119(a) to Japanese Patent Application No. 2015-190860 filed on Sep. 29, 2015. Each of the above application(s) is hereby expressly incorporated by reference, in its entirety, into the present application.

BACKGROUND OF THE INVENTION

1. Field of the Invention

The present invention relates to a cell evaluation apparatus and a cell evaluation method for evaluating cells in a differentiation inducing process.

2. Description of the Related Art

Multipotent stem cells such as induced pluripotent stem (iPS) cells or embryonic stem (ES) cells have an ability of being differentiated into cells of various tissues, and attracts attention as applicability to regenerative medicine, development of medicines, explication of diseases, or the like.

Differentiation inducing is performed to obtain desired cells such as nerve cells or liver cells from multipotent stem cells. In the differentiation inducing, it is necessary to automatically check whether the multipotent stem cells have been correctly differentiated into the desired cells.

Accordingly, in the related art, a method for defining a likelihood of desired cells as an image feature value and detecting and evaluating the image feature value using a discrimination part to automatically check whether multipotent stem cells are differentiated into desired cells has been proposed.

Further, JP2005-168360A has proposed a method for determining a cell differentiation stage on the basis of a reduction rate of the amount of oxygen that is dissolved in a culture medium, and the amount of alkaline phosphatase. Further, JP2006-042663A and WO2010/137722A have proposed a method for checking whether multipotent stem cells are in an undifferentiated state or in a differentiated state by analyzing an expression level of genes relating to differentiation.

SUMMARY OF THE INVENTION

However, for example, in a method for detecting an image feature value using a single discrimination part to evaluate whether multipotent stem cells have differentiated into the desired cells, it is not possible to evaluate whether a region where the desired cells are not detected using the discrimination part is a region where cells other than the desired cells are present or a region where cells are not present.

Accordingly, for example, even in a case where it is possible to detect differentiated cells using the discrimination part, there is a possibility that undifferentiated cells remain in a region where the differentiated cells are not detected. In this way, in a case where the undifferentiated cells remain, there is a problem in that the undifferentiated cells become a malignant tumor after tissues are transplanted.

Further, JP2005-168360A, JP2006-042663A and WO2010/137722A disclose methods for evaluating a differentiated state of cells, but even if the disclosed methods are used, there is a possibility that remaining undifferentiated cells are overlooked.

The invention has been made in consideration of the above-mentioned problems, and an object of the invention is to provide a cell evaluation apparatus and a cell evaluation method capable of preventing overlooking of remaining undifferentiated cells.

According to an aspect of the invention, there is provided a cell evaluation apparatus comprising: a first evaluation part and a second evaluation part that evaluate cells to be evaluated, in which the first evaluation part includes at least two discrimination parts that respectively discriminate whether the cells to be evaluated correspond to at least two types of cells on the basis of an image obtained by imaging the cells to be evaluated, and the second evaluation part evaluates the cells to be evaluated under an evaluation condition different from an evaluation condition of the first evaluation part in a case where discrimination results in at least two discrimination parts among the discrimination parts are conflicting.

In the cell evaluation apparatus according to this aspect of the invention, the second evaluation part may evaluate the cells to be evaluated on the basis of an image obtained by imaging the cells to be evaluated at a magnification higher than that in the first evaluation part.

In the cell evaluation apparatus according to this aspect of the invention, in a case where the evaluation is performed on the basis of images obtained by dividing a group of the cells to be evaluated into a plurality of regions, the second evaluation part may set an evaluation result of one image among the images of the plurality of regions as a representative evaluation result.

In the cell evaluation apparatus according to this aspect of the invention, in a case where the evaluation is performed on the basis of images obtained by dividing a group of the cells to be evaluated into a plurality of regions, the second evaluation part may set the most common evaluation result among evaluation results of the images of the plurality of regions as a representative evaluation result.

In the cell evaluation apparatus according to this aspect of the invention, in a case where the evaluation is performed on the basis of images obtained by dividing a group of the cells to be evaluated into a plurality of regions, the second evaluation part may set a result obtained by averaging evaluation results of the images of the plurality of regions as a representative evaluation result.

In the cell evaluation apparatus according to this aspect of the invention, the first evaluation part may evaluate the cells to be evaluated on the basis of an image obtained by imaging the cells to be evaluated using a non-invasive imaging method, and the second evaluation part may evaluate the cells to be evaluated on the basis of an image obtained by imaging the cells to be evaluated using an invasive imaging method.

In the cell evaluation apparatus according to this aspect of the invention, the second evaluation part may evaluate the cells to be evaluated on the basis of a fluorescent image of the cells to be evaluated.

In the cell evaluation apparatus according to this aspect of the invention, the second evaluation part may evaluate the cells to be evaluated on the basis of an image captured at a time point when a preset time elapses from an imaging time point of the image used for the discrimination in the first evaluation part.

In the cell evaluation apparatus according to this aspect of the invention, the second evaluation part may evaluate the cells to be evaluated on the basis of a larger number of images, obtained by imaging the cells to be evaluated, than those in the first evaluation part.

In the cell evaluation apparatus according to this aspect of the invention, in a case where the first evaluation part and the second evaluation part evaluate the cells to be evaluated over time plural times, and previous discrimination results in the at least two discrimination parts in the first evaluation part are conflicting, evaluation of cells to be currently evaluated may not be performed in the first evaluation part, and may be performed in the second evaluation part.

In the cell evaluation apparatus according to this aspect of the invention, in a case where the first evaluation part and the second evaluation part divide a group of the cells to be evaluated into a plurality of regions to perform the evaluation, and previous discrimination results in one region among the plurality of regions are conflicting, evaluation of cells to be currently evaluated in the one region and regions around the one region may not be performed in the first evaluation part.

In the cell evaluation apparatus according to this aspect of the invention, the second evaluation part includes at least two discrimination parts, similarly to the first evaluation part, and in a case where discrimination results in the at least two discrimination parts are conflicting, the cells to be evaluated may be evaluated under a further different evaluation condition.

In the cell evaluation apparatus according to this aspect of the invention, in a case where the discrimination results in the at least two discrimination parts included in the second evaluation part are conflicting, the second evaluation part may change the evaluation condition plural times to sequentially perform the evaluation, and may terminate the evaluation at a time point when the discrimination results in the at least two discrimination parts become consistent results.

According to another aspect of the invention, there is provided a cell evaluation method comprising: performing a first evaluation for discriminating, on the basis of an image obtained by imaging cells to be evaluated, whether the cells to be evaluated correspond to at least two types of cells using at least two discrimination parts; and performing a second evaluation for evaluating the cells to be evaluated under an evaluation condition different from an evaluation condition of the first evaluation in a case where discrimination results in at least two discrimination parts among the discrimination parts are conflicting.

According to the cell evaluation apparatus and the cell evaluation method of the invention, a first evaluation for discriminating, on the basis of an image obtained by imaging cells to be evaluated, whether the cells to be evaluated correspond to at least two types of cells is performed using at least two discrimination parts, and a second evaluation for evaluating the cells to be evaluated is performed under an evaluation condition different from an evaluation condition of the first evaluation in a case where discrimination results in at least two discrimination parts among the discrimination parts are conflicting. Accordingly, for example, even in a case where it is discriminated that cells to be evaluated correspond to differentiated cells using one discrimination part, in a case where it is discriminated that the cells to be evaluated correspond to undifferentiated cells using the other discrimination part, since discrimination results thereof are conflicting, the second evaluation is performed again under a different evaluation condition. Accordingly, it is possible to prevent overlooking of remaining undifferentiated cells by re-evaluating as described above.

BRIEF DESCRIPTION OF THE DRAWINGS

FIG. 1 is a block diagram showing a schematic configuration of a cell evaluation system using an embodiment of a cell evaluation apparatus of the invention.

FIG. 2 is a table showing discrimination results in a first discrimination part, discrimination results in a second discrimination part, and determination results of cells based on the discrimination results.

FIG. 3 is a diagram showing an imaging region and evaluation target ranges obtained by dividing the imaging region.

DESCRIPTION OF THE PREFERRED EMBODIMENTS

Figure 4:
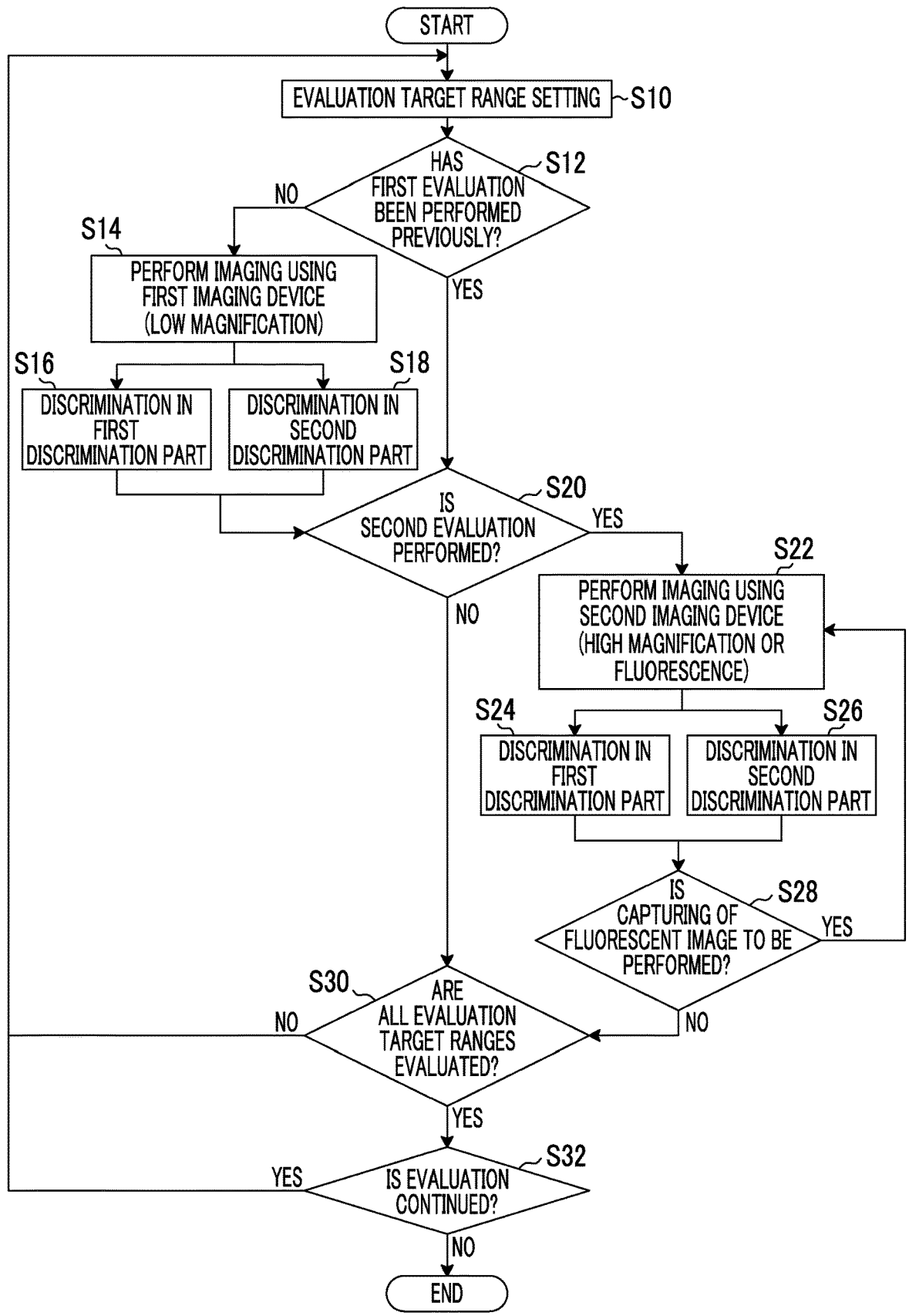
FIG. 4 is a flowchart illustrating an operation of the cell evaluation system using the embodiment of the cell evaluation apparatus of the invention.

Hereinafter, a cell evaluation system using an embodiment of a cell evaluation apparatus and a cell evaluation method according to the invention will be described in detail with reference to the accompanying drawings. FIG. 1 is a block diagram showing a schematic configuration of a cell evaluation system using a cell evaluation apparatus of this embodiment.

The cell evaluation system of this embodiment includes a first evaluation part 1 and a second evaluation part 2, as shown in FIG. 1. The first evaluation part 1 includes a first imaging device 10, and the second evaluation part includes a second imaging device 20. The first evaluation part 1 and the second evaluation part 2 share a discrimination result evaluation device 30. Further, a display device 3 and an input device 4 are connected to the discrimination result evaluation device 30.

The first imaging device 10 captures an image of cells in a differentiation inducing process. In this embodiment, a phase difference microscope is used as the first imaging device 10. The first imaging device 10 includes an imaging element such as a charge-coupled device (CCD) image sensor or a complementary metal-oxide semiconductor (CMOS) image sensor, and a captured image captured by the imaging element is output to the discrimination result evaluation device 30 from the first imaging device 10.

As cells that are imaging targets, for example, cells in a process where multipotent stem cells such as induced pluripotent stem (iPS) cells or embryonic stem (ES) cells are differentiation-induced to mesoderms, cells in a process where nerve stem cells are differentiation-induced to neurons, cells in a process where liver stem cells are differentiation-induced to liver cells, cells in a process where multipotent stem cells are differentiation-induced to cardiomyocytes, cells in a process where hematopoietic stem cells are differentiation-induced to red blood cells, lymphocytes, or platelets, or the like are used, but the invention is not limited thereto, and other cells in a differentiation inducing process may be used.

The second imaging device 20 captures an image of cells in a differentiation inducing process, similar to the first imaging device 10. Here, the second imaging device 20 images the cells under an evaluation condition different from that in the first imaging device 10. The evaluation condition includes an imaging condition. Specifically, the second imaging device 20 of this embodiment captures a phase difference image of a magnification higher than that in the first imaging device 10, and is configured to be able to capture a fluorescent image. While the capturing of the phase difference image is performed using a non-invasive imaging method, the capturing of the fluorescent image is performed using an invasive imaging method since there is damage of cells due to irradiation of excitation light. Further, the second imaging device 20 may perform imaging using fluorescence emitted from dyed cells, or may perform imaging using self-emission of cells. The captured image captured by the second imaging device 20 is output to the discrimination result evaluation device 30 from the second imaging device 20.

The discrimination result evaluation device 30 is configured of a computer that includes a central processing unit (CPU), a semiconductor memory, a hard disk, or the like. The discrimination result evaluation device 30 determines, on the basis of images captured by the first imaging device 10 and the second imaging device 20, whether cells included in the captured images are undifferentiated cells or differentiated cells.

Specifically, the discrimination result evaluation device 30 includes a first discrimination part 31, a second discrimination part 32, and a discrimination result determination part 33.

The first discrimination part 31 discriminates whether cells included in a captured image are undifferentiated cells on the basis of the input captured image. As a method for discriminating whether the cells are the undifferentiated cells, for example, a method for performing discrimination using morphological characteristics of the cells may be used.

Specifically, for example, it is possible to discriminate whether cells are undifferentiated cells using the size, circularity, or brightness of each cell. Further, a method for discriminating whether cells are a colony of undifferentiated cells in a cell colony unit instead of a cell unit may be used. For example, a method for discriminating whether cells are undifferentiated cells using the number or density of cells included in a cell colony, the circularity or brightness of the cell colony, the area or density of white streaks in the cell colony, or the like, may be used.

The white streaks represent boundaries of cells, a so-called halo image. In a case where differentiation continues, halos increase. Thus, in a case where the area or density of white streaks is equal to or lower than a threshold value, it may be determined that the cells are undifferentiated cells. Further, as a method for discriminating whether cells are undifferentiated cells, other known techniques may be used.

The second discrimination part 32 discriminates whether cells included in a cell image are differentiated cells on the basis of the input captured image. As a method for discriminating whether the cells are the differentiated cells, for example, a method for performing discrimination using morphological characteristics of the cells after differentiation may be used.

Specifically, for example, in a case where a nerve stem cell is differentiation-induced to neurons, it is possible to use the size, circularity or brightness of the cell, the lengths or the number of axons, the sizes or the number of dendrons, the sizes or the number of cell nuclei, the sizes or the density of white streaks, or the like. Further, in a case where a liver stem cell is differentiation-induced to liver cells, it is possible to use the size, circularity or brightness of each cell, the sizes or the number of cell nuclei, the area or density of white streaks, or the like. In addition, in a case where a multipotent stem cell is differentiation-induced to myocardial cells, the presence or absence of pulsation of cells, the area or density of white streaks, or the like may be used. The presence or absence of pulsation of the cells may be acquired by calculating a variation of two images captured in time series. Furthermore, in a case where a hematopoietic stem cell is differentiation-induced to red blood cells, it is possible to use colors of the cells.

As a method for discriminating whether cells are differentiated cells, other various techniques may be used. Further, as a discrimination method in the first discrimination part 31 and the second discrimination part 32, a discrimination method based on the size, circularity, brightness of each cell, or the area or density of white streaks is commonly used, but discrimination criteria such as threshold values in the first discrimination part 31 and the second discrimination part 32 are different from each other.

The discrimination result determination part 33 acquires a discrimination result in the first discrimination part 31 and a discrimination result in the second discrimination part 32, and determines whether the discrimination results are conflicting. Specifically, as shown in FIG. 2, in a case where the discrimination result in the first discrimination part 31 is a discrimination result indicating that undifferentiated cells are present in a captured image and the discrimination result in the second discrimination part 32 is a discrimination result indicating that differentiated cells are not present in the captured image, since the results are not conflicting, it is determined that the cells in the captured image are undifferentiated cells, as appropriate results.

Further, in a case where the discrimination result in the first discrimination part 31 is a discrimination result indicating that undifferentiated cells are not present in a captured image and the discrimination result in the second discrimination part 32 is a discrimination result indicating that differentiated cells are present in the captured image, since the results are not conflicting, it is determined that the cells in the captured image are differentiated cells, as appropriate results.

On the other hand, in a case where the discrimination result in the first discrimination part 31 is a discrimination result indicating that undifferentiated cells are present in a captured image and the discrimination result in the second discrimination part 32 is a discrimination result indicating that differentiated cells are present in the captured image, since the results are conflicting, determination on whether the cells in the captured image are differentiated cells or undifferentiated cells is unclear.

Further, in a case where the discrimination result in the first discrimination part 31 is a discrimination result indicating that undifferentiated cells are not present in a captured image and the discrimination result in the second discrimination part 32 is a discrimination result indicating that differentiated cells are not present in the captured image, since the results are conflicting, determination on whether the cells in the captured image are differentiated cells or undifferentiated cells is unclear. The discrimination result determination part 33 stores the above-described determination result.

A whole controller 34 controls the entirety of the cell evaluation system including the first imaging device 10 and the second imaging device 20. Particularly, in a case where the determination result in the discrimination result determination part 33 is unclear, the whole controller 34 performs a control so that imaging of cells in the second imaging device 20 is performed under an evaluation condition different from that of the first imaging device 10, and so that discrimination in the first discrimination part 31 and discrimination in the second discrimination part 32 are performed again.

The imaging in the second imaging device 20 may be automatically performed according to the determination result by the whole controller 34, or may be performed by causing the display device 3 to display the fact that the determination result is unclear to notify a user of the result and causing the user to input a command for performing the imaging in the second imaging device 20 using the input device 4.

The second imaging device 20 images cells under an evaluation condition different from that of the first imaging device 10 as described above, on the basis of a control signal output from the whole controller 34, and in this case, captures a phase difference image of the cells at a magnification higher than that in the first imaging device 10.

The image captured at the high magnification by the second imaging device 20 is output to the discrimination result evaluation device 30, and the discrimination result evaluation device 30 performs discrimination in the first discrimination part 31 and discrimination in the second discrimination part 32 again, on the basis of the input high magnification image. Further, the discrimination result determination part 33 determines whether the cells included in the captured image are undifferentiated cells, differentiated cells, or obscure on the basis of the discrimination results, and stores the determination result.

Further, in a case where the determination result in the discrimination result determination part 33 is unclear again, the whole controller 34 performs a control so that imaging of cells in the second imaging device 20 is performed under a further different evaluation condition, and so that discrimination in the first discrimination part 31 and discrimination in the second discrimination part 32 are performed again. Specifically, the second imaging device 20 performs imaging for a fluorescent image of cells. The imaging for the fluorescent image in the second imaging device 20 may be automatically performed according to the determination result by the whole controller 34, or may be performed by causing the display device 3 to display the fact that the determination result is unclear to notify a user of the result and causing the user to input a command for performing the imaging in the second imaging device 20 using the input device 4.

The fluorescent image captured by the second imaging device 20 is output to the discrimination result evaluation device 30, and the discrimination result evaluation device 30 performs determination in the first discrimination part 31 and determination in the second discrimination part 32 again, on the basis of the input fluorescent image. Further, the discrimination result determination part 33 determines whether the cells included in the captured image are undifferentiated cells, differentiated cells, or obscure, on the basis of the discrimination results, and stores the determination result.

The first imaging device 10 and the second imaging device 20 scan the inside of an imaging region R where a plurality of cells is present, as shown in FIG. 3, under the control of the whole controller 34, and captures an image of each divided evaluation target range r in the imaging region R. The unit of the imaging region R may be set to a well plate having a plurality of wells, for example, and each well in the well plate may be set to the evaluation target range r. Alternatively, one well may be set to the imaging region R, and each divided region in the one well may be set to the evaluation target range.

The determination in the discrimination result evaluation device 30 is performed on the basis of the image of each evaluation target range r, and a determination result for each evaluation target range r is stored in the discrimination result determination part 33.

The display device 3 is configured of a display device such as a liquid crystal display. The display device 3 displays images captured by the first imaging device 10 and the second imaging device 20 under the control of the whole controller 34, or displays discrimination results in the first and second discrimination parts 31 and 32 and a determination result in the discrimination result determination part 33.

The input device 4 is configured of an input device such as a keyboard or a mouse. The input device 4 receives an input of a command for imaging in the second imaging device 20 as described above, for example. The display device 3 and the input device 4 may be configured of a touch panel so that the touch panel functions as both the display device 3 and the input device 4.

Next, an operation of the cell evaluation system of this embodiment will be described with reference to a flowchart shown in FIG. 4.

First, a cultivation container in which cells to be evaluated in a differentiation inducing process are contained is placed in the first imaging device 10, and a setting is performed so that an image of the initial evaluation target range is captured (S10).

Further, it is confirmed by the whole controller 34 whether a first evaluation is previously performed with respect to the set evaluation target range (S12). The first evaluation refers to a process from imaging in the first imaging device 10 to storaging of a determination result in the discrimination result determination part 33.

Further, in a case where it is confirmed that the first evaluation is not previously performed (NO in S12), a phase difference image of the initial evaluation target range is captured using the first imaging device 10 (S14), and the captured image is input to the first discrimination part 31 and the second discrimination part 32. The first imaging device 10 performs imaging at a magnification lower than that in the second imaging device 20, and specifically, performs imaging at a magnification of 1 to 4.

Then, it is discriminated by the first discrimination part 31 whether undifferentiated cells are present in the captured image (S16), and it is discriminated by the second discrimination part 32 whether differentiated cells are present in the captured image (S18). The respective discrimination results are input to the discrimination result determination part 33.

Further, the discrimination result determination part 33 determines whether the cells in the captured image are undifferentiated cells, differentiated cells, or obscure on the basis of the discrimination results in the first and second discrimination parts 31 and 32, and stores the determination result.

The whole controller 34 determines whether a second evaluation is to be performed on the basis of the determination result in the discrimination result determination part 33 (S20). Specifically, in a case where the determination result in the discrimination result determination part 33 is unclear, the whole controller 34 determines that the second evaluation is to be performed, and in other cases, the whole controller 34 terminates the evaluation of the initial evaluation target range without performing the second evaluation (NO in S20). The second evaluation refers to a process from imaging in the second imaging device 20 to storaging of the determination result in the discrimination result determination part 33.

Further, in a case where it is determined by the whole controller 34 that the performing of the second evaluation is to be determined (YES in S20), the cultivation container is placed in the second imaging device 20, a phase difference image of the initial evaluation target range is captured by the second imaging device 20 (S22), and the captured image is input to the first discrimination part 31 and the second discrimination part 32. The second imaging device 20 performs imaging at a magnification higher than that in the first imaging device 10, specifically, performs imaging at a magnification of 10 to 20, for example. Movement of the cultivation container from the first imaging device 10 to the second imaging device 20 may be performed using, for example, a turn table, or the like.

Then, it is discriminated again by the first discrimination part 31 whether undifferentiated cells are present in the captured image (S24), and it is discriminated again by the second discrimination part 32 whether differentiated cells are present in the captured image (S26). Then, the respective discrimination results are input to the discrimination result determination part 33.

Further, the discrimination result determination part 33 determines whether the cells in the captured image are undifferentiated cells, differentiated cells, or obscure on the basis of the discrimination results in the first and second discrimination parts 31 and 32, and stores the determination result.

The whole controller 34 determines whether evaluation based on a fluorescent image is to be performed on the basis of the determination result in the discrimination result determination part 33 (S28). Specifically, in a case where the determination result in the discrimination result determination part 33 is unclear, the whole controller 34 determines that the evaluation based on the fluorescent image is to be performed, and in other cases, the whole controller 34 terminates the evaluation of the initial evaluation target range (NO in S28).

Further, in a case where the whole controller 34 determines that the evaluation based on the fluorescent image is to be performed (YES in S28), the fluorescent image of the initial evaluation target range is captured by the second imaging device 20 (S22), and then, the fluorescent image is input to the first discrimination part 31 and the second discrimination part 32.

Then, it is discriminated again by the first discrimination part 31 whether undifferentiated cells are present in the fluorescent image (S24), and it is discriminated again by the second discrimination part 32 whether differentiated cells are present in the fluorescent image (S26). Then, the discrimination results are input to the discrimination result determination part 33.

Further, the discrimination result determination part 33 determines whether the cells in the fluorescent image are undifferentiated cells, differentiated cells, or obscure on the basis of the discrimination results in the first and second discrimination parts 31 and 32, stores the determination result, and then, terminates the evaluation of the initial evaluation target range (NO in S28).

As described above, the evaluation is performed three times at the maximum with respect to the initial evaluation target range, and the determination results are stored.

Further, in a case where the next evaluation target range is present (NO in S30), a cultivation container is placed in the first imaging device 10 again, and a setting is performed so that an image of the next evaluation target range is captured (S10). In a similar way to the initial evaluation target range, the evaluation is performed three times at the maximum with respect to the next evaluation target range, and the determination results are stored.

Then, the evaluation target ranges are sequentially changed, and the processes of S12 to S30 are repeated. Then, at a time point when the evaluation of all evaluation target ranges is terminated, the evaluation of the current imaging region R is terminated (YES in step S30).

Further, in a case where a predetermined period elapses and after differentiation inducing of the cells is proceeded and again continuously evaluation of the imaging region R is performed (YES in S32), the procedure returns to S10, the second-round evaluation is performed again in the order from the initial evaluation target range in the imaging region R. Here, in a case where the first evaluation has already been performed previously and it is confirmed that the determination result in the discrimination result determination part 33 shows that the cells are either undifferentiated cells or differentiated cells and does not show that the cells are obscure, no evaluation is performed (YES in S12, and NO in S20). On the other hand, in a case where the first evaluation has already been performed previously and the determination result in the discrimination result determination part 33 shows that the cells are obscure, the first evaluation is not performed, and evaluation starts from the second evaluation (YES in S12, and YES in S20).

Further, at a time point when evaluation of all the evaluation target ranges for which determination results are unclear is terminated, the second-round evaluation in the imaging region R is terminated (YES in S30).

Then, in a case where a predetermined period further elapses and after differentiation inducing of the cells is proceeded and the third-round evaluation of the imaging region R is performed (YES in S32), the procedure returns to S10, and the same processes as in the case of the second-round evaluation in the imaging region R are repeated.

On the other hand, in a case where a user inputs a command for discontinuing the third-round evaluation in the imaging region R, or at a time point when determination results in all the evaluation target ranges r in the imaging region R are confirmed and an evaluation target range r for which the determination result is unclear is not present, the process is terminated (NO in S32).

According to the cell evaluation system of the above-described embodiment, it is discriminated whether cells to be evaluated correspond to undifferentiated cells or differentiated cells on the basis of an image obtained by imaging the cells to be evaluated, respectively, using the first and second discrimination parts 31 and 32, and in a case where discrimination results in the first and second discrimination parts 31 and 32 are conflicting, the cells to be evaluated are re-evaluated under a different evaluation condition. Accordingly, by re-evaluating as described above, it is possible to prevent overlooking of remaining undifferentiated cells.

In the above-described embodiment, in a case where the determination result based on the evaluation in the first evaluation part 1 is unclear, the evaluation in the second evaluation part 2 is immediately performed, but the evaluation may be performed by the second evaluation part 2 at a time point when a predetermined time elapses after the evaluation is performed by the first evaluation part. That is, at a time point when the predetermined time elapses from imaging for an image in the first imaging device 10, imaging for an image in the second imaging device 20 may be performed. In this case, since it may be considered that differentiation of cells continues with the lapse of time and states of the cells vary, as in the above-described embodiment, it is not essential to change a magnification, and the imaging in the second imaging device 20 may be performed at a low magnification.

Further, in the above-described embodiment, a phase difference image of a high magnification and a fluorescent image are captured using the second imaging device 20, but the invention is not limited thereto, and for example, imaging for a plurality of phase difference images having different exposure times may be performed, and discrimination in the first and second discrimination parts 31 and 32 may be performed using an image obtained by adding up the plurality of phase difference images. Further, in the second imaging device 20, a multiple exposure image may be captured, or a confocal image may be captured. Further, in the second imaging device 20, two images having different imaging conditions may be captured, and discrimination in the first and second discrimination parts may be performed using a difference image.

Further, in the above-described embodiment, in a case where evaluation after the second round with respect to the imaging region R is performed, with respect to an evaluation target range r for which the first evaluation was performed previously and a determination result is unclear, the first evaluation is not performed and evaluation starts from the second evaluation, but with respect to peripheral evaluation target ranges r that are adjacent to the evaluation target range r, similarly, evaluation may start from the second evaluation without performing the first evaluation. This is because there is a high possibility that the peripheral evaluation target ranges r that are adjacent to the evaluation target range r for which the determination result is unclear also have unclear determination results. Thus, by starting evaluation from the second evaluation as described above, it is possible to reduce time for evaluation of the imaging region R.

Figure 5:
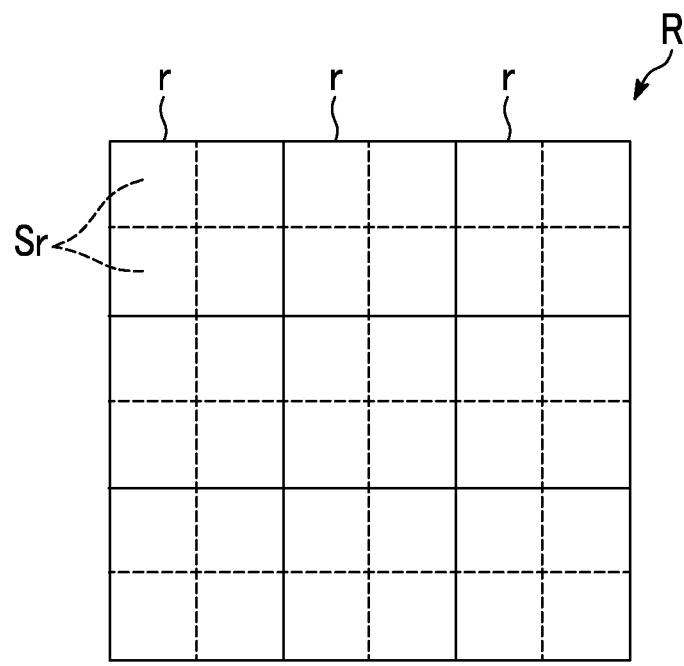
FIG. 5 is a diagram showing an imaging region, evaluation target ranges obtained by dividing the imaging region, and divided regions obtained by dividing the evaluation target ranges.

In addition, in the above-described embodiment, in a case where high magnification imaging is performed in the second imaging device 20, an imaging visual field becomes narrow. Thus, a result that an image for each of divided regions sr obtained by dividing the evaluation target range r into a plurality of regions is captured is obtained, as shown in FIG. 5. In this case, in a case where determination results with respect to the images of the respective divided regions are different from each other, a determination result of an image of any one divided region sr among the plurality of divided regions sr may be stored as a representative determination result of the evaluation target range r.

Alternatively, the most common determination result among the determination results of the images of the plurality of divided regions sr included in the evaluation target range r may be stored as a representative determination result of the evaluation target range r.

Alternatively, an average determination result of the determination results of the images of the plurality of divided region sr included in the evaluation target range r may be stored as a representative determination result of the evaluation target range r.

Specifically, for example, the first discrimination part 31 calculates a likelihood of undifferentiated cells with respect to cells in an image of each divided region sr as a first score, and calculates an average value of the first scores in the entire divided regions sr. Further, similarly, the second discrimination part 32 calculates a likelihood of differentiated cells with respect to cells in an image of each divided region sr as a second score, and calculates an average value of the second scores in the entire divided regions sr. The first score has a larger value as a possibility that the cells are undifferentiated cells is higher (the likelihood of the undifferentiated cells is high), and the second score has a larger value as a possibility that the cells are differentiated cells is higher (the likelihood of the differentiated cells is high).

Further, it is determined whether the average values are conflicting by comparing the average value of the first scores with the average value of the second scores, and the determination result is stored as a representative determination result of the evaluation target range r. Specifically, in a case where a difference between the average value of the first scores and the average value of the second scores is larger than a predetermined threshold value, it is considered that the average values are not conflicting, and a determination result having a larger average value is used as the determination result of the evaluation target range r. On the other hand, in a case where the difference between the average value of the first scores and the average value of the second scores is smaller than the predetermined threshold value, it is considered that the average values are conflicting and the determination result of the evaluation target range r is unclear.

With respect to the score of the likelihood of the undifferentiated cells and the score of the likelihood of the differentiated cells, as described above, low-dimensional information such as the size, brightness, or color of each cell may be scored, for example, or high-dimensional information in cytology such as the circularity of each cell, the shape of a nucleus of the cell, or the density of the cells may be scored.

Alternatively, in a case where even one unclear determination result is included among the determination results with respect to the images of the plurality of divided regions sr included in the evaluation target range r, it may be considered that the determination result with respect to the evaluation target range r is unclear, and the result may be stored.

Further, in the above-described embodiment, in the second evaluation part 2, evaluation based on a high magnification phase difference image and evaluation based on a fluorescent image are performed, but in the evaluation based on the fluorescent image, in a case where discrimination results in the first and second discrimination parts 31 and 32 are conflicting, the evaluation may be performed on the basis of images captured under further different evaluation conditions, and the evaluation may be terminated at a time point when the discrimination results in the first and second discrimination parts 31 and 32 are not conflicting.

In addition, in the above-described embodiment, evaluation of whether cells to be evaluated are undifferentiated cells or differentiated cells is performed, but the invention is not limited thereto, and evaluation of whether cells to be evaluated are live cells or dead cells may be performed.

Specifically, the first discrimination part 31 may discriminate whether cells to be evaluated are live cells, the second discrimination part 32 may discriminate whether the cells to be evaluated are dead cells, and the discrimination result determination part 33 may determine whether the cells to be evaluated are live cells, dead cells, or obscure. The discrimination of whether the cells to be evaluated are the live cells may be performed on the basis of circularity, brightness, or the like, for example, and the discrimination of whether the cells to be evaluated are the dead cells may be performed on the basis of the brightness or the presence or absence of a nucleus, for example. A phase difference image of the dead cells generally becomes white, and becomes an image with a high brightness. In this way, by evaluating whether cells to be evaluated are live cells or dead cells, it is possible to appropriately remove the dead cells.

Further, evaluation of whether cells to be evaluated are multipotent stem cells or feeder cells may be performed. Specifically, the first discrimination part 31 may discriminate whether cells to be evaluated are multipotent stem cells, the second discrimination part 32 may discriminate whether the cells to be evaluated are feeder cells, and the discrimination result determination part 33 may determine whether the cells to be evaluated are multipotent stem cells, feeder cells, or obscure. The discrimination of whether the cells to be evaluated are the multipotent stem cells may be performed on the basis of circularity, brightness, or the like, for example, and the discrimination of whether the cells to be evaluated are the feeder cells may be performed on the basis of unique shapes of the feeder cells, for example. In this way, by evaluating whether cells to be evaluated are multipotent stem cells or feeder cells, it is possible to appropriately remove the feeder cells at a time point when differentiation-inducing is terminated.

Furthermore, in the above-described embodiment, cells to be evaluated are evaluated using discrimination results in two discrimination parts of the first discrimination part 31 and the second discrimination part, but instead, the cells to be evaluated may be evaluated using discrimination results in three or more discrimination parts. Specifically, for example, a configuration in which a third discrimination part is provided with respect to the above-described embodiment and the third discrimination part discriminates whether cells to be evaluated are feeder cells may be used. In a case where discrimination results in two or more discrimination parts among the first to third discrimination parts are conflicting, and in a case where all the discrimination parts have discrimination results indicating that there are no cells of a corresponding type, re-evaluation in the second evaluation part 2 may be performed. Even in a case where four or more discrimination parts are provided, conditions of re-evaluation are the same.

EXPLANATION OF REFERENCES

1: first evaluation part
2: second evaluation part
3: display device
4: input device
10: first imaging device
20: second imaging device
30: discrimination result evaluation device
31: first discrimination part
32: second discrimination part
33: discrimination result determination part
34: whole controller

What is claimed is:

1. A cell evaluation apparatus comprising:
a central processing unit that performs a first evaluation and a second evaluation that evaluate cells to be evaluated,
wherein the central processing unit is configured to:
evaluate whether the cells to be evaluated correspond to at least two types of cells using at least two discriminations that respectively discriminate on the basis of an image obtained by imaging the cells to be evaluated, as the first evaluation, and
evaluate the cells to be evaluated under an evaluation condition different from an evaluation condition of the first evaluation in a case where discrimination results in at least two discriminations among the at least two discriminations of the first evaluation are conflicting, as the second evaluation.

2. The cell evaluation apparatus according to claim 1, wherein the central processing unit evaluates the cells to be evaluated on the basis of an image obtained by imaging the cells to be evaluated at a magnification higher than that in the first evaluation, as the second evaluation.

3. The cell evaluation apparatus according to claim 2, wherein in a case where the second evaluation is performed on the basis of images obtained by dividing a group of the cells to be evaluated into a plurality of regions, the central processing unit sets an evaluation result of one image among the images of the plurality of regions as a representative evaluation result.

4. The cell evaluation apparatus according to claim 3, wherein the central processing unit
evaluates the cells to be evaluated on the basis of an image obtained by imaging the cells to be evaluated using a non-invasive imaging method, as the first evaluation, and
evaluates the cells to be evaluated on the basis of an image obtained by imaging the cells to be evaluated using an invasive imaging method, as the second evaluation.

5. The cell evaluation apparatus according to claim 4, wherein the central processing unit evaluates the cells to be evaluated on the basis of a fluorescent image of the cells to be evaluated, as the second evaluation.

6. The cell evaluation apparatus according to claim 2, wherein in a case where the second evaluation is performed on the basis of images obtained by dividing a group of the cells to be evaluated into a plurality of regions, the central processing unit sets the most common evaluation result among evaluation results of the images of the plurality of regions as a representative evaluation result.

7. The cell evaluation apparatus according to claim 6, wherein the central processing unit
evaluates the cells to be evaluated on the basis of an image obtained by imaging the cells to be evaluated using a non-invasive imaging method, as the first evaluation, and
evaluates the cells to be evaluated on the basis of an image obtained by imaging the cells to be evaluated using an invasive imaging method, as the second evaluation.

8. The cell evaluation apparatus according to claim 2, wherein in a case where the second evaluation is performed on the basis of images obtained by dividing a group of the cells to be evaluated into a plurality of regions, the central processing unit sets a result obtained by averaging evaluation results of the images of the plurality of regions as a representative evaluation result.

9. The cell evaluation apparatus according to claim 8, wherein the central processing unit
evaluates the cells to be evaluated on the basis of an image obtained by imaging the cells to be evaluated using a non-invasive imaging method, as the first evaluation, and
evaluates the cells to be evaluated on the basis of an image obtained by imaging the cells to be evaluated using an invasive imaging method, as the second evaluation.

10. The cell evaluation apparatus according to claim 2, wherein the central processing unit evaluates the cells to be evaluated on the basis of an image obtained by imaging the cells to be evaluated using a non-invasive imaging method, as the first evaluation, and evaluates the cells to be evaluated on the basis of an image obtained by imaging the cells to be evaluated using an invasive imaging method, as the second evaluation.

11. The cell evaluation apparatus according to claim 10, wherein the central processing unit evaluates the cells to be evaluated on the basis of a fluorescent image of the cells to be evaluated, as the second evaluation.

12. The cell evaluation apparatus according to claim 1, wherein the central processing unit evaluates the cells to be evaluated on the basis of an image obtained by imaging the cells to be evaluated using a non-invasive imaging method, as the first evaluation, and evaluates the cells to be evaluated on the basis of an image obtained by imaging the cells to be evaluated using an invasive imaging method, as the second evaluation.

13. The cell evaluation apparatus according to claim 12, wherein the central processing unit evaluates the cells to be evaluated on the basis of a fluorescent image of the cells to be evaluated, as the second evaluation.

14. The cell evaluation apparatus according to claim 1, wherein the central processing unit evaluates the cells to be evaluated on the basis of an image captured at a time point when a preset time elapses from an imaging time point of the image used for the discrimination in the first evaluation-part, as the second evaluation.

15. The cell evaluation apparatus according to claim 1, wherein the central processing unit evaluates the cells to be evaluated on the basis of a larger number of images, obtained by imaging the cells to be evaluated, than those in the first evaluation, as the second evaluation.

16. The cell evaluation apparatus according to claim 1, wherein in a case where the central processing unit performs the first evaluation and the second evaluation over time plural times, and previous discrimination results in the at least two discriminations in the first evaluation are conflicting, the central processing unit does not perform an evaluation of cells to be currently evaluated in the first evaluation but performs an evaluation of cells to be currently evaluated in the second evaluation.

17. The cell evaluation apparatus according to claim 16, wherein in a case where the central processing unit divides a group of the cells to be evaluated into a plurality of regions to perform the evaluation in the first evaluation and the second evaluation, and previous discrimination results in one region among the plurality of regions are conflicting, an evaluation of cells to be currently evaluated in the one region and regions around the one region is not performed in the first evaluation.

18. The cell evaluation apparatus according to claim 1, wherein the central processing unit evaluates using at least two discriminations which are the same as the first evaluation in the second evaluation, and in a case where discrimination results in the at least two discriminations of the second evaluation are conflicting, the central processing unit evaluates the cells to be evaluated under a new evaluation condition which is other than the evaluation condition of the first evaluation and the evaluation condition of the second evaluation, as a new evaluation.

19. The cell evaluation apparatus according to claim 18, wherein in a case where the discrimination results in the at least two discriminations included in the second evaluation are conflicting, the central processing unit changes the new evaluation condition plural times to sequentially perform the new evaluation under the new evaluation condition, and terminates the new evaluation at a time point when the discrimination results in the at least two discriminations of the new evaluation become consistent results.

20. A cell evaluation method comprising:

performing a first evaluation for discriminating, on the basis of an image obtained by imaging cells to be evaluated, whether the cells to be evaluated correspond to at least two types of cells using at least two discrimination parts; and performing a second evaluation for evaluating the cells to be evaluated under an evaluation condition different from an evaluation condition of the first evaluation in a case where discrimination results in at least two discrimination parts among the at least two discrimination parts of the first evaluation are conflicting.

* * * * *